United States Patent [19]
Price et al.

[11] Patent Number: 6,013,206
[45] Date of Patent: Jan. 11, 2000

[54] PROCESS FOR THE FORMATION OF HIGH ASPECT RATIO LIPID MICROTUBULES

[75] Inventors: Ronald R. Price, Stevensville, Md.; Joel M. Schnur, Burke; Paul E. Schoen, Alexandria, both of Va.; Dan Zabetakis, College Park, Md.; Mark Spector, Springfield, Va.

[73] Assignee: The United States of America as represented by the Secretary of the Navy, Washington, D.C.

[21] Appl. No.: 09/080,194

[22] Filed: May 18, 1998

[51] Int. Cl.⁷ .............................. B01J 13/02; B01J 13/04
[52] U.S. Cl. .................... 264/4.1; 264/4.6; 428/402.2; 428/402.24; 427/213.31
[58] Field of Search ................. 264/4.1, 4.6; 428/402.2, 428/402.24; 427/213.31

[56] References Cited

U.S. PATENT DOCUMENTS

| 4,877,501 | 10/1989 | Schnur et al. . |
| 4,911,981 | 3/1990 | Schnur et al. ................ 428/402.24 |
| 4,990,291 | 2/1991 | Schoen et al. ...................... 264/4.7 |
| 5,705,191 | 1/1998 | Price et al. ........................... 424/473 |

*Primary Examiner*—Nathan M. Nutter
*Attorney, Agent, or Firm*—Barry A. Edelberg; Romulo H. Delmendo

[57] ABSTRACT

Lipid microtubules having a controlled bilayer structure and high aspect ratio are formed in a methanol/ethanol/water solvent system. The lipid microtubules may then be catalyzed (e.g., with a palladium/tin catalyst) in an acidified catalytic bath having no more than about 30 g of catalytic salts. These catalyzed microtubules are then metallized using a diluted plating bath with replenishment of the plating bath as needed to obtain the desired metallization thickness.

7 Claims, 2 Drawing Sheets

PROCESS FOR THE FORMATION OF HIGH ASPECT RATIO LIPID MICROTUBULES

BACKGROUND OF THE INVENTION

1. Field of the Invention

The present invention relates generally to lipid microtubules and more specifically to lipid microtubules having a high aspect ratio.

2. Description of the Background Art

The production of lipid microstructures has previously been described in U.S. Pat. Nos. 4,877,501, 4,911,291 and 4,990,291, and U.S. Ser. No. 08/703,608, filed Aug. 27, 1996 by Price et al, the entireties of all of which are incorporated herein by reference for all purposes. The methods use an alcohol and water phase for the production of lipid microcylinders by direct crystallization. None of these patents teach an optimum method for producing very high aspect ratio lipid microcylinders (typically above about an average aspect ratio of about 20, and commonly having an average aspect ratio of about 50 or more), at high yield rates (e.g., at about 50 or higher) and then preserving that high aspect ratio during subsequent processing steps.

Currently, the alcohol and water mixed solvent bath that may be varied over a very wide range of concentrations to produce lipid microcylinders from a polymerizable lecithin. These methods address the use of a single alcohol and do not predict the activity of mixed solvents, the effect of mixed solvents on the morphology of the resulting microcylinders, or the effect of mixed solvents on the process yield.

In current methods control of the number of lipid bilayers is achieved by varying the alcohol/water concentration as well as the lipid concentration. This control of the number of lipid bilayers is described in U.S. Ser. No. 08/703,608, the entirety of which is incorporated herein by reference. However, no method exists for production of microcylinders at very high aspect ratios while at the same time preserving bilayer numbers between 2 and 4. At low concentrations the bilayer walls are single bilayers and as concentration increases the number of bilayers increases.

Previously described methodologies that produce high aspect ratio lipid microstructures have resulted in single walled microcylinders at such high numbers that the solutions are highly thixotropic, thus frustrating attempts at further processing without so much shearing of the resultant tubules that they become useless for further metallic plating.

Also, previous methods of electroplating lipid tubules often degraded the aspect ratios and/or cause the lipid tubules to "clump" or "weld".

SUMMARY OF THE INVENTION

Accordingly, it is an object of this invention to produce lipid microtubules having a high aspect ratio.

It is another object of the present invention to produce metal-plated microtubules having a high aspect ratio.

It is a further object of the present invention to provide high aspect ratio uncoated or metal-coated microtubules in high yield.

It is yet another object of the present invention to provide high aspect ratio lipid microtubules having a well-defined bilayer structure.

These and additional objects of the invention are accomplished by forming the lipid microtubules from a solution of lipid in a methanol/ethanol/water solvent system. Once formed, the lipid microtubules are suspended and catalyzed in an acidic bath that is either free of catalytic salts or has a low concentration of catalytic salts. The catalyzed microtubules fall out of suspension. The catalyzed tubules are resuspended in a large volume of water and a dilute solution of an electroless plating is bath added. After plating is complete, the microtubules are isolated and washed.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1A:
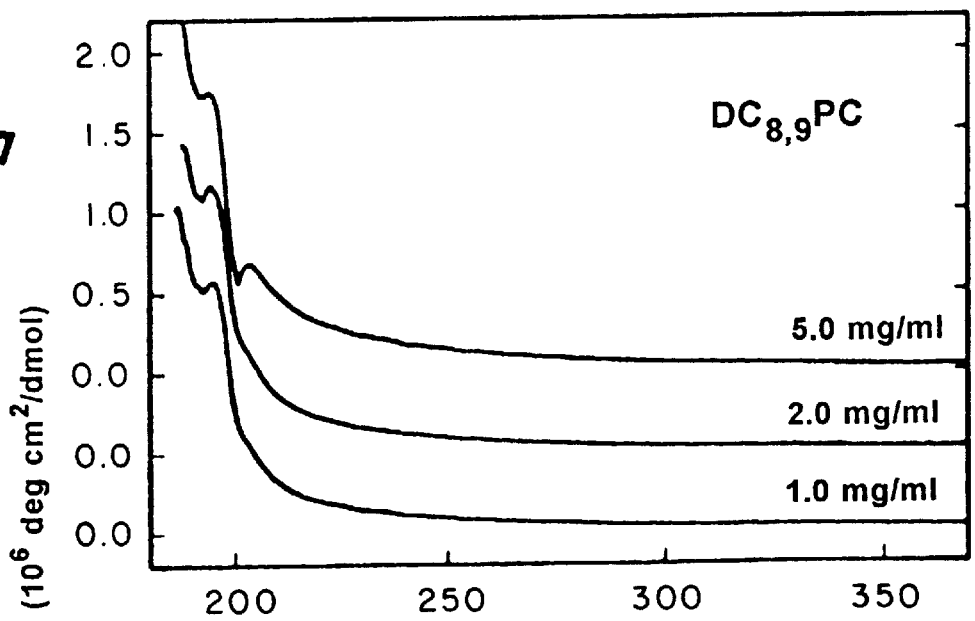
FIGS. 1a and 1b show the concentration dependence of the CD spectra for two diacetylenic lipids.

The present invention uses self-assembling microtubule-forming lipids and mixtures of such lipids. Typically, self-assembling microtubule-forming lipids are diacetylenic lipids, such as chiral phosphatidylcholines, and mixtures of these diacetylenic lipids. Lipids useful in the method of the present invention are described in U.S. Pat. Nos. 4,877,501, 4,911,291 and 4,990,291. In all of the processing steps of the present invention, the fragility of the unclad lipid tubule structure should be kept in mind. Thus, it is generally desirable to avoid sudden changes in the system (e.g., concentration, thermal changes, osmolarity changes) or significant stirring that might give rise to physical stresses in the system and resultant tubule damage. The addition of solvents and other materials, as well as temperature changes, should be accomplished gradually to minimize stress on the system and the formed or nascent lipid tubules therein.

The solvent system used in the present invention is a mixture of water and an alcoholic component formed of a methanol and ethanol mixture. The methanol and water should preferably first be filtered to remove any particulate material. Typically, methanol will be from about 50 to about 95 vol %, more often about 50 to about 90 vol %, of the alcoholic component, with the remainder being ethanol. The most typical alcoholic component is an 80/20 v/v methanol/ethanol mixture. An overabundance of the methanol component forms single bilayer tubules. These single bilayer tubules are too fragile for further processing. An overabundance of ethanol wastes lipid by forming thick, highly multilayer tubules.

Typically, the solvent system will be about 60 to about 90 vol percent total alcohol with the remainder being water. Most often, the total solvent system is an 80/20 alcohol/water mixture. If the concentration of water is too high, structures precipitate too quickly and form heterogeneous shapes, especially short tubules. If the concentration of alcohol is too great, the lipid component stays in solution, i.e. no tubules or any other structures form.

The concentration of the lipids within the solvent system should be sufficiently low to avoid tubule aggregation. An overly dilute concentration of lipids, while workable, however, wastes solvent. Typically, the concentration of lipid in the solvent system is about 0.1 mg/ml to about 10 mg/ml. More often, the concentration of lipid in the solvent system is about 3 to about 8 mg/ml total solvent, and is most often about 2.5 and 5.0 mg/ml total solvent.

In a preferred process, the selected lipid or lipid mixture is dissolved in pure methanol by gradual addition to volume of methanol that has been preheated to at least about 5° C. greater than the lipids chain melting transition temperature in the solvent system of choice. The temperature, of course, should be sufficiently low to avoid lipid degradation. The amount of pure methanol used in this step should be a smaller volume than that to which the methanol/lipid will later be added to form the methanol/ethanol/water/lipid solution. The amount of methanol used for this step, however, should be sufficient to fully dissolve the lipid or lipids.

A mixture of methanol, ethanol, and water are also thoroughly mixed and heated to a temperature at least about 5° C. greater than the lipid's chain melting transition temperature in the final methanol/ethanol/water solvent system. Again, the temperature should be sufficiently low to avoid lipid degradation. The composition of this methanol/ethanol/water mixture is selected so that, upon addition of the methanol/lipid solution, the final methanol/ethanol/water solvent system will have the desired methanol/ethanol volume ratio and the desired alcohol/water ratio, as well as the desired concentration of lipid.

The methanol/lipid solution is then gradually added to the methanol/ethanol/water mixture. Typically, it is useful to filter the resulting solution of lipid in methanol/ethanol/water to remove particulate matter. Filtration may be accomplished, for example, by passing the solution through a Nucleopore™ membrane (e.g., 0.22 micron). The solution of lipid in methanol/ethanol/water is then gently mixed to assure good distribution of the lipid throughout without disrupting or breaking any nascent lipid chains or microtubules.

This multistep lipid dissolution procedure assures that the lipids are not exposed to sudden changes that might cause disruption or degradation of the lipids If one wishes to accept a somewhat lower yield in favor of simplified procedure, the lipid may be added in a single step to a premade methanol/ethanol/water solvent system having the desired ratios of methanol to ethanol and water to alcohol.

After complete dissolution and distribution of the lipid in the methanol/ethanol/water solvent, the temperature of the solution is slowly lowered to a formation temperature below the exothermic transition temperature. Typically, the temperature is lowered at a rate of less than about 1° C. per hour, to enhance uniformity of temperature and/or concentration, thus minimizing the risk of disrupting the growth of nascent tubules. The formation temperature is typically more than 10° C. below the exothermic transition temperature of the lipid. Other than the freezing point of the solution, no lower temperature limit is imposed upon the formation temperature. Of course, using a formation temperature significantly less than that need for good tubule formation wastes time and energy. Typically, the formation temperature is about 15° C. to about 35° C., and typically about 20° C. to about 35° C. below the lipid's exothermic transition temperature. The solution is held at the formation temperature for between about 24 hours or longer. Once the tubule structures are formed they are stable as long as the tubule structures are not heated above the endothermic transition temperature.

The above temperature reduction is typically accomplished in three or more steps. In the first step, the temperature of the lipid solution is lowered to a temperature about 1 to about 5° C. (and typically about 2° C. to about 4° C., and most often about 3° C.) below the exothermic transition temperature of the lipid. The lipid solution is then gently stirred to eliminate any further temperature or concentration gradient to provide for a uniform solution for the self-assembly or crystallization phase of tubule formation. Following mixing, the solution is further gradually cooled (typically at a rate of less than about 1° C. per hour) to a temperature of about 7 to about 15° C. (e.g., about 30° C.±0.5° C.) below the exothermic transition temperature. The solution is maintained at that temperature for about 24 hours. Then, the temperature of the solution is further gradually cooled (typically at a rate of less than about 1° C. per hour) to the formation temperature. Typically, this final cooling step cools the solution by at least about 5° C., and more often cools the solution by about 5 to about 20° C. In a typical procedure using $DC_{89}PC$ as the lipid, the exothermic transition temperature is about 43° C., the temperature of the lipid solution is first gradually lowered (e.g., over a period of 16 hours) typically about 40° C., the lipid solution is then gradually cooled to about 30±0.5° C. and held at 30±0.5° C. for at least 24 hours, and the temperature of the lipid solution is then gradually cooled (over a period of about 24 hours) to the final formation temperature of about 10–20° C.

After formation, the lipid microtubules are removed from the solution, for example by very gentle filtration through low speed centrifugation, or by counter flow dialysis to remove the alcohol solvents. The dialysis must be sufficiently slow so as to eliminate any localized effects due to the heat of mixing of the ethanol/methanol and water. Rapid dialysis or mixing with water results in violent interaction of the alcohol and water resulting in disruption of the lipid structures, and if excessive heat of mixing effects are resultant then the tubules will likewise be dissolved or malformed.

The present invention also includes a method for catalyzation of the lipid microstructures in which the use of acidic salts is reduced or eliminated. Lipid salts disrupt bilayer integrity by interactions with the headgroups of the lipid and the resulting disruption of the bilayer crystalline structure. To eliminate the use of these salts it is necessary to add dilute mineral acid (e.g., HCl or $H_2SO_4$) to the tubule suspension in such a way as to lower the pH to 1.0 without undue heating of the mixture. The methodology is to add sufficient dilute mineral acid (e.g., up to about 0.5M HCl, typically about 0.2M) in water in such a manner that the tubule/water suspension is brought to a final pH suitable for binding of the catalyst to the microtubules. At too high of a pH, undesirable large Pd complexes form. If the pH is too low, the catalyst will not bind the microtubules or the tubules will be destroyed. Typically, this pH is about 0.5 to about 1.5, and is most typically about 1.0.

The catalyst (typically a commercial palladium tin catalyst, although other catalysts such as palladium alone, may also work) is then typically used as follows. For every 1 liter of tubule/water suspension (after settling of the tubules, not including the volume of the supernatant) about 10 liters of catalyst bath is utilized. The use of acidic salts is restricted to 30 g per liter (typically no more than about 20 g per liter) of the catalytic bath that is made up at about 5% by volume commercial bath concentrate (example: Shipley Cataposit 44™). There is no lower limit on the concentration of catalyst in the catalytic bath. Nevertheless, unnecessarily low concentrations of catalyst will waste time, space, and solvent. Too high of a concentration of catalyst will needlessly complicate catalyst removal, requiring large volumes of deionized water for dilution and washing after plating. As stated earlier, an overly high concentration of catalytic salts disrupts the structure of the lipid microtubules.

The catalyst is slowly added to the lipid microtubule suspension in such a way as to prevent any rapid change in osmolarity of the bath that might damage the lipid microtubules. The addition is best unaccompanied by agitation of any kind to the suspension to prevent vertical or horizontal sheer from disrupting the lipid microcylinders. Diffusion will distribute the catalyst if added at the top of the batch container slowly and uniformly over the surface area. After the lipids have been catalyzed, the lipid microtubules slowly settle to the bottom of the bath due to an increase in specific gravity due to the bound catalyst. The supernatant is then drawn off and is replaced with dilute acid (e.g., 0.1 M HCl, and generally about 0.01 to about 0.25 M) to dilute unbound catalyst. The slight acidity assists in preventing precipitation of the unbound catalyst. Alternatively, unbound catalyst may be removed by dialysis. Typically, the resulting suspension is once again allowed to settle and the supernatant is again drawn off, resulting in serial dilution of the catalyst. After the tubules have resettled, a gradual flow of deionized water into the bath removes the smaller tubules and remaining unbound catalyst. The flow of water may be stopped once sufficient unbound catalyst has been removed to avoid difficulties that might arise during the subsequent electroplating step (such as precipitation of metal complexes in the plating solution. Typically, the flow of water washes the microtubules with a volume of deionized water equal to or greater than about twice the bath volume. Serial dilution and gradual water flow (and/or dialysis) removes unbound catalytic salts and small, undesired tubules without causing large changes in osmolarity or thermal gradients that might result in tubule damage.

Typically, the catalyst bound to the microtubules is palladium, but it may be other materials, such as platinum or gold. More specifically, it is preferred to sensitize the lipid microstructure by attachment of a palladium/tin (Pd/Sn) colloidal catalyst precursor to the surface of the lipid microstructure.

The present invention also provides for a method to electrolessly plate the microtubules with a metallic coating to render them mechanically more robust and conductive. To achieve such a coating without breakage of the microtubules it is necessary to prevent the rapid evolution of hydrogen bubbles (a natural byproduct of the plating chemistry). Rapid evolution will cause pressure to build within the microtubules, thus bursting them. In addition large gas bubbles offer a surface attractive to the microtubules which then rise within the plating bath to aggregate and then become "welded" together by the plating process where they touch forming large aggregates that are difficult to redisperse.

The catalyzed microtubules are suspended in a large volume of water sufficient to produce a volume of 10X the original suspension volume of the naturally settled tubules. Following this step, the plating bath is added slowly, typically as follows. A solution of the plating bath is added to the dilute suspension such that the final concentration reaches about 5 to about 25% (typically about 10%) of that customarily used for plating surfaces. The standard dilution of a plating bath can vary depending on the commercial plating bath selected. For each plating bath selected, however, the manufacturer provides a standard (i.e., customary) plating bath dilution. If desired, about 0.025% by weight K-90 grade poly(vinylpyrollodone) (PVP) may be added to the bath to further reduce the possibility of cold welding and clumping of the high aspect ratio microstructures. If used, the poly (vinylpyrollodone) should first be reacted with a metal salts solution to prevent the PVP from stripping metal ions from the plating bath, thus having an adverse effect on the plating bath performance. Using the plating method described herein, however, the use of PVP is generally not needed to prevent cold welding and clumping.

Once the plating process has been observed to initiate, additional additions of plating bath are added so that the final concentration of the plating bath is reached after 9 further additions. When the reaction appears to subside a sample of the tubules are observed by microscopy to ensure that the coating is not less than 100 nm or meets process requirements. If the desired coating thickness has not yet been achieved, the plating bath is replenished to provide the aforementioned final concentration and plating is continued until the reaction again subsides. Obtaining a thickness of 100 nm or greater generally requires the addition of a total 6X or less of the recommended amount of plating solution for plating printed circuit boards. Serial addition of the plating solution maintains the desired low concentration of plating solution throughout the plating process. The use of an amount of plating bath greater than that required for plating to the desired thickness should be avoided, since excess metal salts would remain in solution following attainment of sufficient thickness. Following plating, the microtubules are either filtered from solution (preferred method) or allowed to settle and the excess bath drawn off. The plated tubules are then rinsed repeatedly with water until all plating salts have been removed. The tubules are then treated with a surface passivating agent, such as a suspension of a silane (e.g., hexamethyldisilizane), ethylene glycol, or a sugar to prevent undue oxidation.

A uniform suspension of the microtubules may be maintained by adding a concentration of surfactant effective to disperse the microtubules, e.g., 0.025% polyvinylpyrollodone. Other surfactants, such as Triton-X100™ should also be effective dispersants. If dehydration of the metallic microtubules is necessary the dispersant is typically removed to prevent it from crashing out of solution and binding the microtubules in an undispersable clump.

Having described the invention, the following examples are given to illustrate specific applications of the invention including the best mode now known to perform the invention. These specific examples are not intended to limit the scope of the invention described in this application.

EXAMPLES

Materials and Methods

The L-enantiomer, 1,2-bis(tricosa-10,12-diynoyl)-sn-glycero-3-phosphocholine (L-DC$_{8,9}$PC), was purchased from JP Laboratory (Middlesex, N.J.). The D-enantiomer (D-DC$_{8,9}$PC) was synthesized by hydrolyzing 2,3-bis (palmitoyl)-sn-glycero-1-phosphocholine (D-DPPC, Sigma Chemical Co.) with tetrabutylammonium hydroxide to form D-glycerophosphocholine, followed by reaction with tricosa-10,12-diynoic anhydride in the presence of 4-N,N-dimethylaminopyridine.[11,19] Other lipids were synthesized by reacting L-glycerophosphocholine with the appropriate diacetylenic anhydride. The L designation has been dropped when referring to these lipids for brevity. Diacetylenic fatty acids were synthesized by coupling the appropriate ω-alkynoic acid with iodoalkynes following the procedure of Singh, A.; Schnur, J. M. *Synth. Commun.* 1986, 16, 847–852 (incorporated by reference herein in its entirety for all purposes), with the exception of tricosa-10,12-diynoic acid which was purchased from Farchan Laboratories (Gainesville, Fla.). All lipids were purified by column chromatography using silica gel and checked for purity by thin-layer chromatography using a chloroform/methanol/water (65:25:4, v/v/v) solvent system in both cases. The purified lipids were a white powder. Tubules were prepared by dissolving the lipid in HPLC-grade methanol or ethanol (Sigma) and mixing with Milli-Q water (Millipore Corp.) at 65° C. On cooling the solution at 3° C./hr through the transition temperature, tubules were formed. CD studies were performed on a Jasco J-720 spectropolarimeter operated between 175 and 600 nm. Solvent absorption limited the effective range of study to above 188 nm. Samples were placed in water-jacketed quartz cells with path lengths of 0.1 to 0.5 mm, with temperature control supplied by a water circulator (Neslab) providing thermal stability of about 0.2° C. The spectrometer was calibrated with ammonium-d-camphorsulfonate ($[\theta]_{291}$=7910 deg cm$^2$/dmol) and D-pantoyllactone ($[\theta]_{219}$=−16140 in water, $[\theta]_{223}$=−12420 in methanol). Samples for electron microscopy were negative stained with 1% uranyl acetate and examined in a Zeiss EM-10C transmission electron microscope operating at 60 kV.

RESULTS

Figure 1B:
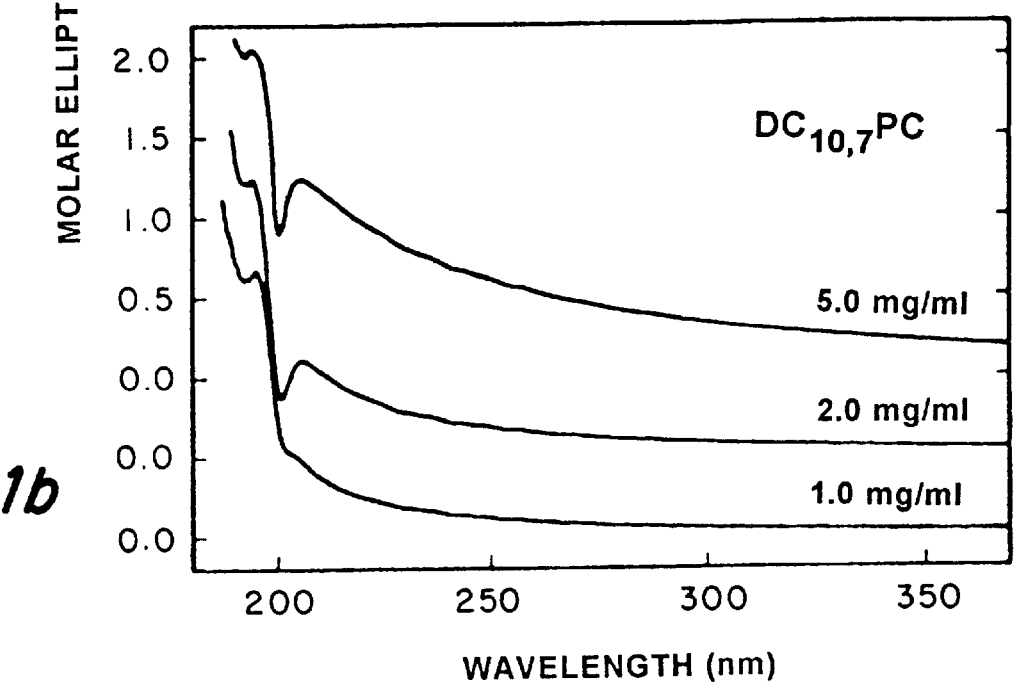

The initial approach to controlling the morphology of diacetylenic lipid tubules was to vary the lipid concentration. It was already known that the thickness of the tubule wall depends on the lipid concentration as well as the alcohol length. Although tubules formed in ethanol/water have multiple-bilayer walls at all lipid concentrations, tubules formed in methanol/water have single-bilayer walls at low lipid concentration, but multiple-bilayer walls at higher lipid concentrations. This increase in thickness is accompanied by an increase in the CD signal at 205 nm. FIGS. 1a and 1b show the concentration dependence of the CD spectra for two diacetylenic lipids. FIG. 1a shows the CD spectra from $DC_{7,9}PC$ tubules in 80:20 (v/v) methanol/water at three different lipid concentrations. The peak at 205 nm is prominent in the 5 mg/ml sample, whereas it only appears as a small elbow in the spectra at lower concentrations. The size of the 195 nm peak is similar at all concentrations. These results suggest a crossover from single-bilayer to multiple-bilayer tubules near a lipid concentration of 5 mg/ml in 80:20 methanol/water. As previously reported, the crossover concentration depends on the methanol/water ratio, with the crossover occurring at higher concentrations as this ratio increases.

Examining the tubule morphology, by transmission-mode electron micrograph, at the crossover concentration, shows that most (>90%) of the tubules have two-bilayer thick walls in a 5 mg/ml sample prepared in methanol/water 85:15. The wall thickness for the two-bilayer tubule in this micrograph was 16±2 nm, implying a single bilayer thickness of about 8 nm. This value was slightly larger than the bilayer thickness of 6.6 nm determined by x-ray diffraction from multi-bilayer tubules. This result may be an artifact of the staining process or may indicate that there is some swelling of the bilayers in these methanol/water tubules. These tubules also exhibit a very high aspect ratio. It was possible to use electroless plating to metallize these two-bilayer tubules, which was not possible with single-bilayer tubules. This approach provided a significant cost savings over metallizing ethanol/water tubules, which typically have ten bilayers. Unfortunately, this process resulted in highly thixotropic suspensions which were difficult to process for large quantity applications. Diluting the sample lead to single bilayer tubules which could not be coated with metal. As discussed below, this problem was overcome through the use of mixed alcohol solvents.

The two-bilayer tubule imaged showed clear helical markings. Such markings are characteristic of multiple-bilayer ethanol/water tubules, but are not seen in single-bilayer methanol/water tubules. These markings may have been associated with defects in the tilt direction of the lipid molecules on the tubules or they may have been the edges of helical ribbons wrapped around the inner tubule core. Although it is sometimes difficult to differentiate the helical markings from the top and bottom bilayers, observation of the tubule ends or taking stereo pairs of micrographs occasionally allows unambiguously the determination of the handedness of the helical markings. Only right-handed helices are observed for the L enantiomer.

Figure 2:
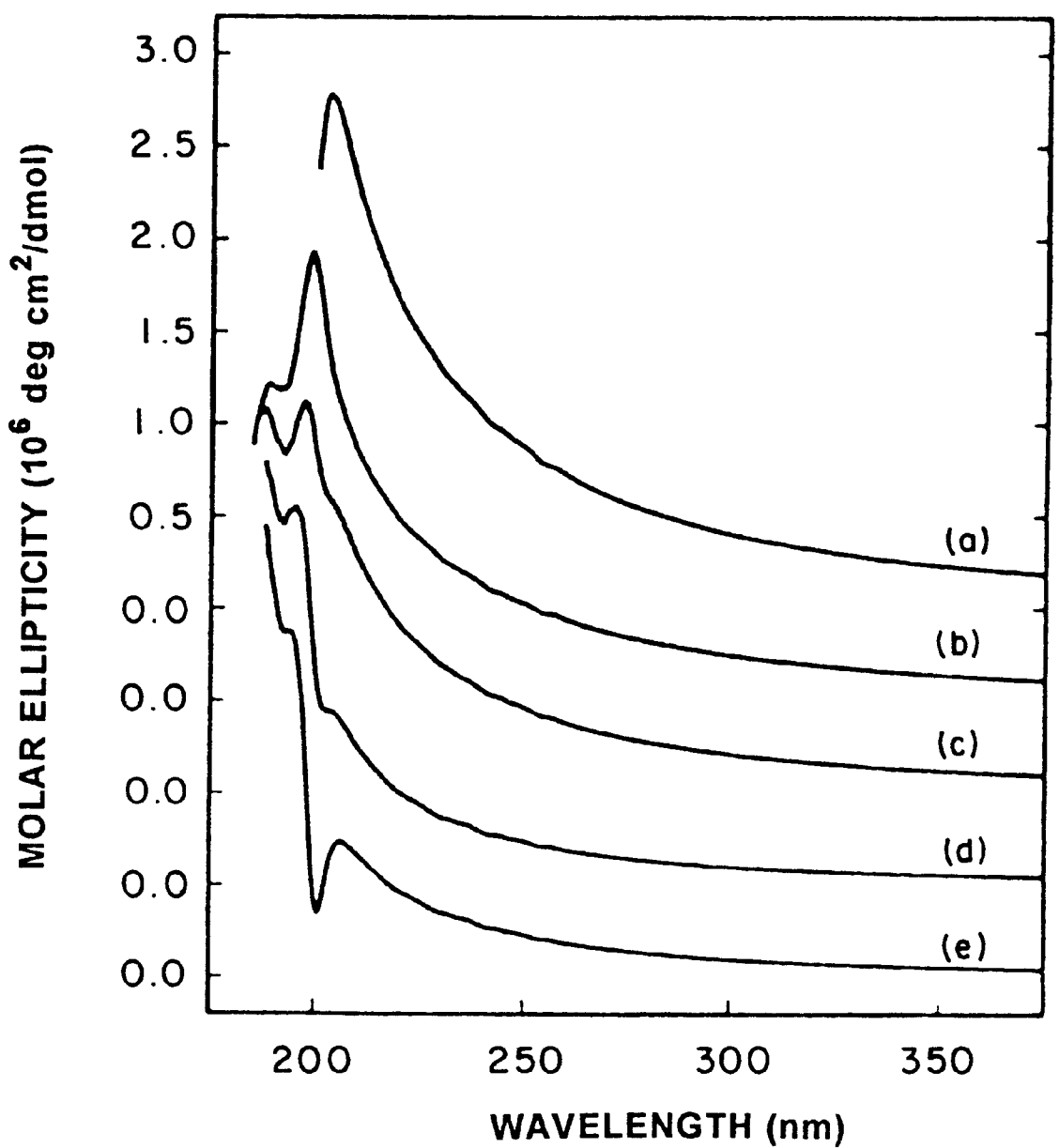
FIG. 2 shows CD spectra of $DC_{8,9}PC$ tubules in these three-component solutions at 25° C. and a lipid concentration of 2 mg/ml.

As a second approach, the morphology of $DC_{8,9}PC$ tubules in solutions containing water and a mixture of alcohols was studied. Tubules were made in solutions of water, methanol, and ethanol, keeping the volume fraction of water fixed at 30% and varying the methanol/ethanol ratio. FIG. 2 shows CD spectra of $DC_{8,9}PC$ tubules in these three-component solutions at 25° C. and a lipid concentration of 2 mg/ml. In the methanol/water (7:3) solution, the CD spectra are characterized by peaks at 205 nm and 195 nm, with another peak below the instrumental cutoff at 188 nm. As ethanol is added to the solution, the 195 nm peak appears to broaden and red-shift slightly. In a solution with equal amounts of methanol and ethanol, the lower peak shifts to 197 nm and the 205 nm peak still appears as a distinct elbow in the data. As shown by an electron micrograph of the tubules formed in this solution, 35:35:30 methanol/ethanol/water, these tubules appear to be quite different than those previously observed. They are composed of a single bilayer inner wall, with no observable helical markings, and another partial bilayer helically wrapped around the outside. Almost all of the tubules observed in this solution have that appearance, although the width of the partial bilayer has a large variance. In the bottom-right corner of this electron micrograph, there appeared some tubules where the partial bilayer was coming unwrapped from the tubule. This may have been an artifact introduced in the drying process.

Mixed alcohol solutions also allowed greater control over tubule thickness to overcome the processing problems described above. By producing tubules in a solution of 64:16:20 methanol/ethanol/water at a lipid concentration of 5 mg/ml, it was possible to obtain very high aspect ratio tubules. TEM analysis showed these tubules contained between 2 and 4 lipid bilayers. This system proved to be less thixotropic and it was possible to process these tubules using electroless plating techniques to obtain long metallized tubules. As shown by an optical micrograph of copper coated tubules prepared in this manner and embedded in an acrylic polymer film, the average length of these tubules was 60 $\mu$m with a standard deviation of 35 $\mu$m. Tubules formed in ethanol/water solutions tended to be thicker than those formed in methanol/ethanol/water and required significant agitation to disperse them during processing. The shear lead to breakage and a decrease in the average length of the metal coated tubules to 15 $\mu$m with a standard deviation of 9 $\mu$m, compared to the corresponding dimensions of metal-coated tubules formed in methanol/ethanol/water. Tubules formed in the 64:16:20 solution were not severely thixotropic and required much less agitation than those formed in ethanol/water. These advantages enabled the production of high aspect ratio (>100:1) metallized tubules.

DISCUSSION

The results of the initial approach to changing tubule morphology, by varying the lipid concentration, were straightforward to interpret and apply. These results show that the thickness of the tubule walls changes gradually as a function of lipid concentration in methanol/water solution. At low concentration the tubules had single-bilayer walls, while at high concentration they had multiple-bilayer walls. Thus, by working close to the crossover concentration, tubules with two-bilayer walls, which are thick enough to be coated with metal but are not so thick that they waste lipid, could be prepared. Although it was possible to metal plate these tubules, the solution proved to be too thick to process on a large scale.

The experiments on tubules in mixed methanol/ethanol/water solutions show that the solvent also had a substantial effect on tubule structure. This effect was too great to be explained by a simple change in the lipid solubility or other physical properties of the solvent. Rather, one must consider effects of alcohol preferentially partitioning to the lipid bilayer interface. This would change the nature of the hydration layer surrounding the bilayer and, thus, alter the spacing and packing of the lipid headgroups. It is also possible that the alcohol entered the bilayer causing a larger change in the molecular packing. Expansion of the intermolecular spacing may have allowed neighboring molecules to rotate more freely with respect to each other. By the theoretical argument of Harris et al., *Phys. Rev. Lett.* 1997, 78, 1476–1479, the entirety of which is incorporated herein by reference for all purposes, this rotation should average out part of the chiral interaction between neighboring molecules, thus reducing the intermolecular order in the membrane. These effects would become stronger when methanol is replaced by ethanol which has a longer acyl chain. Combining the results from variations in lipid concentration with those from mixed alcohol solutions, it was possible to optimize the solution conditions for large quantity processing. Using a solution of 64:16:20 methanol/ethanol/water and a lipid concentration of 5 mg/ml, it was possible to produce high aspect ratio metallized tubules that were not thixotropic.

Obviously, many modifications and variations of the present invention are possible in light of the above teachings. It is therefore to be understood that, within the scope of the appended claims, the invention may be practiced otherwise than as specifically described.

What is claimed is:

1. A method of forming lipid microtubules, comprising the steps of:

dissolving a lipid in a methanol/ethanol/water solvent in which the vol % of methanol is about 50 to about 95 based on the total combined volume of methanol and ethanol, and the total combined vol % of methanol and ethanol is about 60 to about 90, based on the total volume of said methanol/ethanol/water solvent;

allowing lipid microtubules to self-assemble in said methanol/ethanol/water solvent; and separating said formed lipid microtubules from said methanol/ethanol/water solvent.

2. The method of claim 1, wherein said methanol is about 50 to about 90 percent by volume of the alcoholic component.

3. The method of claim 1, wherein said lipid microtubules are formed in said methanol/ethanol/water solvent at a temperature of about 15° C. to about 35° C. below the exothermic transition temperature of said lipid.

4. The method of claim 1, wherein said lipid is dissolved in said methanol/ethanol/water solvent at a temperature of at least about 5° C. above the chain melting transition temperature of said lipid.

5. The method of claim 1, further comprising the steps of:

lowering the temperature of said solution of said lipid in said methanol/ethanol/water solvent from said temperature during said dissolution step to a uniform temperature throughout said solution of about 1° C. to about 5° C. below the exothermic transition temperature of said lipid in said methanol/ethanol/water solvent, said temperature being lowered at a rate of less than about 1° C./hr;

further cooling the temperature of said solution of said lipid in said methanol/ethanol/water solvent from said uniform temperature to a temperature of about 7 to about 15° C. below the exothermic transition temperature of said lipid in said methanol/ethanol/water solvent at a rate of less than about 1° C./hr;

maintaining said solution of said lipid in said methanol/ethanol/water solvent at said temperature of about 7 to about 15° C. below said exothermic transition temperature for at least about 24 hrs; and additionally cooling said solution of said lipid in said methanol/ethanol/water solvent, by at least about 5° C., from said temperature of about 7 to about 15° C. below said exothermic transition temperature to a tubule formation temperature about 15° C. to about 35° C. below said exothermic transition temperature, at a rate of less than about 1° C./hr.

6. The method of claim 1, wherein said lipid is a diacetylenic phospholipid.

7. The method of claim 6, wherein said lipid is 1,2-bis (tricosa-10,12-diynoyl)-sn-glycero-3-phosphocholine.

* * * * *